US007998086B2

(12) United States Patent
Boock et al.

(10) Patent No.: US 7,998,086 B2
(45) Date of Patent: Aug. 16, 2011

(54) TISSUE EXTRACTION AND MACERATION DEVICE

(75) Inventors: Robert J. Boock, Braintree, MA (US); Nathan S. Cauldwell, Attleboro, MA (US); Keith M. Orr, Boston, MA (US)

(73) Assignee: Depuy Mitek, Inc., Raynham, MA (US)

( * ) Notice: Subject to any disclaimer, the term of this patent is extended or adjusted under 35 U.S.C. 154(b) by 0 days.

(21) Appl. No.: 12/569,165

(22) Filed: Sep. 29, 2009

(65) Prior Publication Data

US 2010/0022915 A1 Jan. 28, 2010

Related U.S. Application Data

(62) Division of application No. 10/661,460, filed on Sep. 11, 2003, now Pat. No. 7,611,473.

(51) Int. Cl.
*A61B 10/00* (2006.01)
(52) U.S. Cl. ........ 600/566; 600/562; 600/564; 600/565; 600/567; 600/568
(58) Field of Classification Search .......... 600/562–571; 606/79–85
See application file for complete search history.

(56) References Cited

U.S. PATENT DOCUMENTS

| | | |
|---|---|---|
| 1,337,998 A | 4/1920 | Church |
| 3,604,417 A | 9/1971 | Stolzenberg |
| 3,698,561 A | 10/1972 | Babson |
| 3,810,545 A | 5/1974 | Filz et al. |
| 3,814,079 A | 6/1974 | Le Roy, Sr. |
| 3,937,222 A | 2/1976 | Banko |
| 4,366,822 A | 1/1983 | Altshuler |
| 4,438,769 A | 3/1984 | Pratt et al. |
| 4,469,153 A | 9/1984 | Morrisette |
| 4,553,553 A | 11/1985 | Homann et al. |
| 4,649,919 A | 3/1987 | Thimsen et al. |
| 4,690,672 A | 9/1987 | Veltrup |
| 4,842,578 A | 6/1989 | Johnson et al. |

(Continued)

FOREIGN PATENT DOCUMENTS

EP 0527312 2/1993

(Continued)

OTHER PUBLICATIONS

Canadian Application No. 2480704 dated Mar. 12, 2009, (6 pages).

(Continued)

*Primary Examiner* — Jeffrey G Hoekstra (57) ABSTRACT

Devices and methods are provided for extracting and macerating tissue, and optionally for depositing the tissue onto a tissue scaffold. The device generally includes an outer tube having a substantially open distal end that is adapted to be placed on and preferably to form a seal with a tissue surface, and a shaft rotatably disposed within the outer tube and movable between a first, proximal position in which the shaft is fully disposed within the outer tube, and a second, distal position in which a portion of a distal end of the shaft extends through the opening in the distal end of the outer tube. The device also includes a tissue harvesting tip formed on the distal end of the shaft that is effective to excise a tissue sample when the shaft is moved to the distal position, and a cutting member that is coupled to the shaft at a position proximal to the tissue harvesting tip. The cutting member is effective to macerate a tissue sample excised by the tissue harvesting tip.

19 Claims, 12 Drawing Sheets

U.S. PATENT DOCUMENTS

| | | | |
|---|---|---|---|
| 4,844,064 A | 7/1989 | Thimsen et al. |
| 4,960,130 A | 10/1990 | Guirguis |
| 5,041,138 A | 8/1991 | Vacanti et al. |
| 5,077,012 A | 12/1991 | Guirguis |
| 5,108,381 A | 4/1992 | Kolozsi |
| 5,108,422 A | 4/1992 | Green et al. |
| 5,186,714 A | 2/1993 | Boudreault et al. |
| 5,195,956 A | 3/1993 | Stockmeier et al. |
| 5,197,483 A | 3/1993 | Rogalsky et al. |
| 5,206,023 A | 4/1993 | Hunziker et al. |
| 5,252,301 A | 10/1993 | Nilson et al. |
| 5,269,785 A | 12/1993 | Bonutti |
| 5,333,627 A | 8/1994 | Mehringer et al. |
| 5,338,294 A | 8/1994 | Blake, III |
| 5,370,609 A | 12/1994 | Drasler et al. |
| 5,387,236 A | 2/1995 | Noishiki et al. |
| 5,398,690 A | 3/1995 | Batten et al. |
| 5,403,317 A | 4/1995 | Bonutti |
| 5,489,291 A | 2/1996 | Wiley |
| 5,494,044 A | 2/1996 | Sundberg |
| 5,526,822 A | 6/1996 | Burbank et al. |
| 5,527,330 A | 6/1996 | Tovey |
| 5,551,778 A | 9/1996 | Hauke et al. |
| 5,575,293 A * | 11/1996 | Miller et al. ............ 600/565 |
| 5,593,423 A | 1/1997 | Person et al. |
| 5,649,547 A | 7/1997 | Ritchart |
| 5,694,951 A | 12/1997 | Bonutti |
| 5,759,190 A | 6/1998 | Vibe-Hansen et al. |
| 5,788,667 A | 8/1998 | Stoller |
| 5,804,366 A | 9/1998 | Hu et al. |
| 5,827,305 A | 10/1998 | Gordon |
| 5,871,454 A | 2/1999 | Majlessi |
| 5,871,462 A | 2/1999 | Yoder et al. |
| 5,900,361 A | 5/1999 | Klebe |
| 5,913,859 A | 6/1999 | Shapira |
| 5,944,686 A | 8/1999 | Patterson et al. |
| 5,949,044 A | 9/1999 | Walker et al. |
| 6,010,476 A | 1/2000 | Saadat |
| 6,017,348 A | 1/2000 | Hart et al. |
| 6,022,354 A | 2/2000 | Mercuri et al. |
| 6,053,923 A | 4/2000 | Veca et al. |
| 6,066,153 A | 5/2000 | Lev et al. |
| 6,071,284 A | 6/2000 | Fox |
| 6,110,176 A | 8/2000 | Shapira |
| 6,120,514 A | 9/2000 | Vibe-Hansen et al. |
| 6,135,977 A | 10/2000 | Drasler et al. |
| 6,174,313 B1 | 1/2001 | Bonutti |
| 6,179,840 B1 | 1/2001 | Bowman |
| 6,214,369 B1 | 4/2001 | Grande et al. |
| 6,216,573 B1 | 4/2001 | Moutafis et al. |
| 6,218,182 B1 | 4/2001 | Naughton et al. |
| 6,242,247 B1 | 6/2001 | Rieser et al. |
| 6,280,398 B1 | 8/2001 | Ritchart et al. |
| 6,299,763 B1 | 10/2001 | Ashman |
| 6,325,806 B1 | 12/2001 | Fox |
| 6,352,555 B1 | 3/2002 | Dzau et al. |
| 6,358,252 B1 | 3/2002 | Shapira |
| 6,364,884 B1 | 4/2002 | Bowman et al. |
| 6,375,635 B1 | 4/2002 | Moutafis et al. |
| 6,378,527 B1 | 4/2002 | Hungerford et al. |
| 6,402,766 B2 | 6/2002 | Bowman et al. |
| 6,423,073 B2 | 7/2002 | Bowman |
| 6,436,110 B2 | 8/2002 | Bowman et al. |
| 6,447,517 B1 | 9/2002 | Bowman |
| 6,451,017 B1 | 9/2002 | Moutafis et al. |
| 6,485,436 B1 | 11/2002 | Truckai et al. |
| 6,497,707 B1 | 12/2002 | Bowman et al. |
| 6,511,493 B1 | 1/2003 | Moutafis et al. |
| 6,537,567 B1 | 3/2003 | Niklason et al. |
| 6,543,455 B2 | 4/2003 | Bonutti |
| 6,554,852 B1 | 4/2003 | Oberlander |
| 6,572,578 B1 | 6/2003 | Blanchard |
| 6,669,710 B2 | 12/2003 | Moutafis et al. |
| 6,736,799 B1 | 5/2004 | Erbe et al. |
| D491,807 S | 6/2004 | Cauldwell et al. |
| D494,063 S | 8/2004 | Cauldwell et al. |
| 6,783,532 B2 | 8/2004 | Steiner et al. |
| 6,846,314 B2 | 1/2005 | Shapira |
| 6,852,330 B2 | 2/2005 | Bowman et al. |
| 6,875,442 B2 | 4/2005 | Holy et al. |
| 6,878,338 B2 | 4/2005 | Taylor et al. |
| 6,884,428 B2 | 4/2005 | Binette et al. |
| 6,921,380 B1 | 7/2005 | Epstein et al. |
| 7,115,100 B2 | 10/2006 | McRury et al. |
| 7,270,284 B2 | 9/2007 | Liao et al. |
| 7,611,473 B2 | 11/2009 | Boock et al. |
| 7,794,408 B2 | 9/2010 | Binette et al. |
| 2001/0043918 A1 | 11/2001 | Masini et al. |
| 2002/0007190 A1 | 1/2002 | Wulfman et al. |
| 2002/0029055 A1 | 3/2002 | Bonutti |
| 2002/0045903 A1 | 4/2002 | Bonutti |
| 2002/0052628 A1 | 5/2002 | Bowman |
| 2002/0055755 A1 | 5/2002 | Bonutti |
| 2002/0082631 A1 | 6/2002 | Bonutti |
| 2002/0091401 A1 | 7/2002 | Hellenkamp |
| 2002/0091403 A1 | 7/2002 | Bonutti |
| 2002/0091406 A1 | 7/2002 | Bonutti |
| 2002/0095157 A1 | 7/2002 | Bowman |
| 2002/0099401 A1 | 7/2002 | Bonutti |
| 2002/0099403 A1 | 7/2002 | Yoo |
| 2002/0106625 A1 | 8/2002 | Hung et al. |
| 2002/0119177 A1 | 8/2002 | Bowman et al. |
| 2002/0127265 A1 | 9/2002 | Bowman et al. |
| 2002/0161449 A1 | 10/2002 | Muschler |
| 2002/0169465 A1 | 11/2002 | Bowman et al. |
| 2002/0177802 A1 | 11/2002 | Moutafis et al. |
| 2003/0009237 A1 | 1/2003 | Bonutti |
| 2003/0012805 A1 | 1/2003 | Chen et al. |
| 2003/0032961 A1 | 2/2003 | Pelo et al. |
| 2003/0036801 A1 | 2/2003 | Schwartz et al. |
| 2003/0044444 A1 | 3/2003 | Malaviya et al. |
| 2003/0049299 A1 | 3/2003 | Malaviya et al. |
| 2003/0114875 A1 | 6/2003 | Sjostrom |
| 2003/0114936 A1 | 6/2003 | Sherwood et al. |
| 2003/0147935 A1 | 8/2003 | Binette et al. |
| 2003/0176881 A1 | 9/2003 | Barlev |
| 2003/0212456 A1 | 11/2003 | Lipchitz et al. |
| 2003/0225344 A1 | 12/2003 | Miller |
| 2004/0010320 A1 | 1/2004 | Huckle et al. |
| 2004/0078090 A1 | 4/2004 | Binette et al. |
| 2004/0092992 A1 | 5/2004 | Adams et al. |
| 2004/0097829 A1 | 5/2004 | McRury et al. |
| 2004/0121459 A1 | 6/2004 | Liao et al. |
| 2004/0126405 A1 | 7/2004 | Sahatjian et al. |
| 2004/0134502 A1 | 7/2004 | Mizuno et al. |
| 2004/0138664 A1 | 7/2004 | Bowman |
| 2004/0142861 A1 | 7/2004 | Mansbridge |
| 2004/0146546 A1 | 7/2004 | Gravett et al. |
| 2004/0169311 A1 | 9/2004 | Bonutti |
| 2004/0175408 A1 | 9/2004 | Chun et al. |
| 2004/0193071 A1 | 9/2004 | Binette et al. |
| 2004/0219182 A1 | 11/2004 | Gomes et al. |
| 2004/0243157 A1 | 12/2004 | Connor et al. |
| 2004/0267362 A1 | 12/2004 | Hwang et al. |
| 2005/0014252 A1 | 1/2005 | Chu et al. |
| 2005/0021035 A1 | 1/2005 | Groiso |
| 2005/0038520 A1 | 2/2005 | Binette et al. |
| 2005/0048644 A1 | 3/2005 | Hedrick et al. |
| 2005/0059905 A1 | 3/2005 | Boock et al. |
| 2005/0059986 A1 | 3/2005 | Bowman |
| 2005/0107814 A1 | 5/2005 | Johnston et al. |
| 2005/0113736 A1 | 5/2005 | Orr et al. |
| 2005/0113937 A1 | 5/2005 | Binette et al. |
| 2005/0113938 A1 | 5/2005 | Jamiolkowski et al. |
| 2005/0125077 A1 | 6/2005 | Harmon et al. |
| 2005/0177249 A1 | 8/2005 | Kladakis et al. |
| 2005/0203527 A1 | 9/2005 | Carrison et al. |
| 2005/0222687 A1 | 10/2005 | Vunjak-Novakovic et al. |
| 2005/0232967 A1 | 10/2005 | Kladakis et al. |
| 2005/0234549 A1 | 10/2005 | Kladakis et al. |
| 2006/0100569 A1 | 5/2006 | McRury et al. |
| 2006/0129086 A1 | 6/2006 | McRury et al. |
| 2007/0032740 A1 | 2/2007 | Quick et al. |
| 2007/0239067 A1 | 10/2007 | Hibner |
| 2008/0071192 A1 | 3/2008 | Hynes |
| 2008/0114389 A1 | 5/2008 | Johnston et al. |

| | | | |
|---|---|---|---|
| 2008/0234715 | A1 | 9/2008 | Pesce et al. |
| 2010/0022915 | A1 | 1/2010 | Boock et al. |
| 2010/0280406 | A1 | 11/2010 | Binette et al. |

FOREIGN PATENT DOCUMENTS

| | | |
|---|---|---|
| EP | 1389548 | 2/2004 |
| EP | 1433423 | 6/2004 |
| EP | 1514521 | 3/2008 |
| JP | 3136640 | 6/1991 |
| JP | 2001505460 | 4/2001 |
| JP | 2001524844 | 12/2001 |
| JP | 2003320013 | 11/2003 |
| JP | 2004121167 | 4/2004 |
| WO | WO-9601135 | 1/1996 |
| WO | WO-9824372 A1 | 6/1998 |
| WO | WO-9824373 A1 | 6/1998 |
| WO | WO-9958066 A1 | 11/1999 |
| WO | WO-9959500 | 11/1999 |
| WO | WO-0041648 | 7/2000 |
| WO | WO 2002/015950 | 2/2002 |
| WO | WO-02089722 A1 | 11/2002 |
| WO | WO-03045259 | 6/2003 |
| WO | 2005086874 A2 | 9/2005 |
| WO | WO-2007112751 | 10/2007 |

OTHER PUBLICATIONS

Albrecht, "The Closure of Joint Cartilage Defects by Means of Cartilage Fragments and Fibrin Adhesive," Fortschr. Med. 101 37:1650-1652 (1983).
Canadian Office Action dated Mar. 12, 2009 for Canadian Applicationn No. 2,480,704 ((4 pages).
EP Search Report, Jun. 18, 2009, EP Appln. 09250905.8.
EP Search Report, Jan. 21, 2011, EP Appln. 10179808.
Australian Office Action dated Dec. 16, 2004 for AU Appl. No. 2004201201.
Australian Office Action dated Oct. 17, 2007 for AU Appl. No. 2005242152.
Australian Office Action dated Sep. 4, 2007 for AU Appl. No. 2005229679.
Canadian Office Action dated Feb. 9, 2010 for Canadian Appl. No. 2480704.
Canadian Office Action dated Jul. 17, 2008 for Canadian Appl. No. 2529014.
Canadian Office Action dated Jul. 27, 2010 for Canadian Appl. No. 2462392.
Canadian Office Action dated May 13, 2008 for Canadian Appl. No. 2480704.
Canadian Office Action dated May 21, 2009 for Canadian Appl. No. 2462392.
Canadian Office Action dated Sep. 5, 2007 for Canadian Appl. No. 2529014.
EP Office Action dated Apr. 28, 2010 for EP Appl. No. 09250905.
EP Office Action dated Jun. 25, 2007 for EP Appl. No. 04251843.
EP Office Action dated Nov. 14, 2007 for EP Appl. No. 04255506.
EP Search Report dated Dec. 16, 2004 for EP Appl. No. 04255506.
EP Search Report dated Feb. 22, 2005 for EP Appl. No. 04251843.
EP Search Report dated Jun. 9, 2006 for EP Appl. No. 05257636.
EP Search Report dated Mar. 6, 2006 for EP Appl. No. 05256936.
EP Search Report dated Sep. 16, 2009 for EP Appl. No. 09250905.
Japanese Office Action dated Aug. 24, 2010 for Japanese App. No. 2004-092799.
Japanese Office Action dated Sep. 7, 2010 for Japanese Appl. No. 2004-264265.

* cited by examiner

TISSUE EXTRACTION AND MACERATION DEVICE

CROSS-REFERENCE TO RELATED APPLICATIONS

This application is a divisional of U.S. application Ser. No. 10/661,460 filed Sep. 11, 2003, and entitled "Tissue Extraction and Maceration Device," which is hereby incorporated by reference in its entirety.

FIELD OF THE INVENTION

The present invention relates generally to devices and methods for extracting and macerating tissue.

BACKGROUND OF THE INVENTION

Bone grafts are often used to treat fractures, gaps in bones caused by trauma or infection, revision joint surgery, and oral/maxillofacial surgery. Bone grafts provide a framework into which the host bone can regenerate and heal. Once implanted, the bone cells weave into and through the porous microstructure of the bone graft to support the new tissue, blood cells and soft tissue as they grow to connect fractured bone segments.

The loss or failure of tissue is one of the most frequent and costly problems in human health care. In recent years, grafting has evolved from the initial autograft and allograft preparations to biosynthetic and tissue-engineered living replacements. Tissue engineering enables the growth of transplantable functional tissue replacements starting from samples of autologous cells of the patient. The cells are obtained by harvesting tissue from a patient using a biopsy and then cells are extracted from the tissue sample and cultured to the appropriate numbers in the laboratory. These living cells are then placed in a three-dimensional natural or synthetic scaffold or matrix, and are kept under tissue specific culture conditions to ensure differentiation and tissue maturation. If provided with the appropriate conditions and signals, the cells will secrete various matrix materials to create an actual living tissue that can be used as a replacement tissue to be implanted back into the defective site in the patient.

Current tissue engineering procedures involve a multi-step process. First, a biopsy is performed to remove a tissue sample from a patient's body. A variety of biopsy devices are well known in the art, including, for example, high-pressure fluid jets that are effective to cut and retrieve a tissue sample. Once the biopsy procedure is complete, the tissue sample is then sent to a laboratory, where the tissue is prepared for cell isolation. The isolated cells can then be placed into a three-dimensional scaffold for subsequent growth and eventually implantation back into the patient.

While current procedures have proven effective, they can be very time-consuming and costly. Accordingly, there exists a need for more efficient and effective methods and devices for obtaining and processing a tissue sample. There also remains a need for an improved biopsy device that maximizes cell viability.

SUMMARY OF THE INVENTION

The present invention provides a tissue extraction and maceration device that is designed to effectively remove a viable tissue sample, to control the volume of tissue removed, and to macerate the tissue sample into particles having a predetermined size. In general, the device includes an outer tube having a substantially open distal end that is adapted to be placed on and to form a seal with a tissue surface, and a shaft that is rotatably disposed within the outer tube and that is movable between a first, proximal position in which the shaft is fully disposed within the outer tube, and a second, distal position in which a portion of a distal end of the shaft extends through the opening in the distal end of the outer tube. In one embodiment, a biasing element can be provided for biasing the shaft to the proximal position, and a trigger mechanism can be connected to the shaft to, upon actuation, overcome the biasing force to move the shaft from the proximal position to the distal position.

The device also includes a tissue harvesting tip formed on the distal end of the shaft. The tissue harvesting tip is effective to excise a tissue sample. In one embodiment, the harvesting tip can be a cone-shaped member having a plurality of cutting teeth formed on an outer surface thereof. In another embodiment, the harvesting tip can be a substantially semi-cylindrical housing having a cutting surface formed around a periphery thereof. While the harvesting tip can have a variety of configurations, it is preferably adapted to penetrate tissue to remove a predetermined volume of tissue when the shaft is moved from the proximal position to the distal position.

The device can further include a cutting member coupled to the shaft at a position proximal to the tissue harvesting tip. The cutting member, which is preferably in the form of at least one blade member extending radially from the shaft, is effective to macerate a tissue sample excised by the tissue harvesting tip. Each blade member can have a shape such as, for example, a rectangular shape, a curved shaped, a triangular shape, a square shape, an irregular shape, and combinations thereof.

In another embodiment, the device includes a sizing screen disposed within the outer tube and positioned proximal to the harvesting tip and the cutting member of the shaft. The sizing screen can have several openings formed therein for allowing tissue of a predetermined size to pass therethrough. The openings can optionally be defined by a wall having an upstream edge that is effective to cut tissue having a size greater than the circumference of the openings.

The present invention also provides a method for harvesting a tissue sample using a tissue extraction and preparation device having an outer tube with an open distal end, and a shaft rotatably disposed within the outer tube and including a tissue harvesting tip formed on the distal end thereof and a cutting member coupled to the shaft at a position proximal to the tissue harvesting tip. The method includes the steps of coupling the proximal end of the shaft to a driver mechanism, and positioning the open distal end of the outer tube against a tissue surface at a desired tissue sample site. The driver mechanism is then actuated to effect rotation of the shaft within the outer tube, and the shaft is moved from a proximal position, wherein the harvesting tip of the shaft is disposed within the outer tube, to a distal position, wherein the harvesting tip extends distally from the outer tube, thereby causing the harvesting tip to obtain a tissue sample. The shaft is then returned to the proximal position wherein the tissue sample is macerated by the cutting member. In a further embodiment, the outer tube can be coupled to a tissue dispensing device that is effective to deposit the macerated tissue sample onto a tissue scaffold.

BRIEF DESCRIPTION OF THE DRAWINGS

The invention will be more fully understood from the following detailed description taken in conjunction with the accompanying drawings, in which like reference numerals designate like parts throughout the various figures, and wherein.

DETAILED DESCRIPTION OF THE INVENTION

Figure 1A:
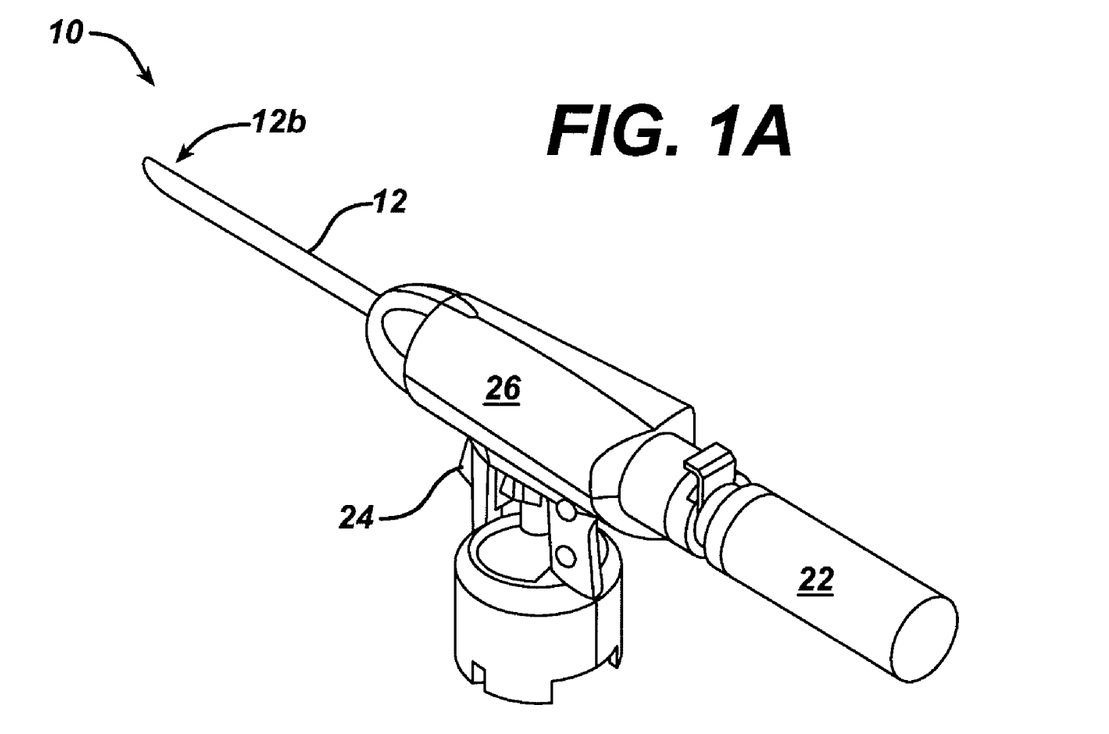
FIG. 1A is a perspective view of a tissue extraction and maceration device according to one embodiment of the present invention.
Figure 1B:
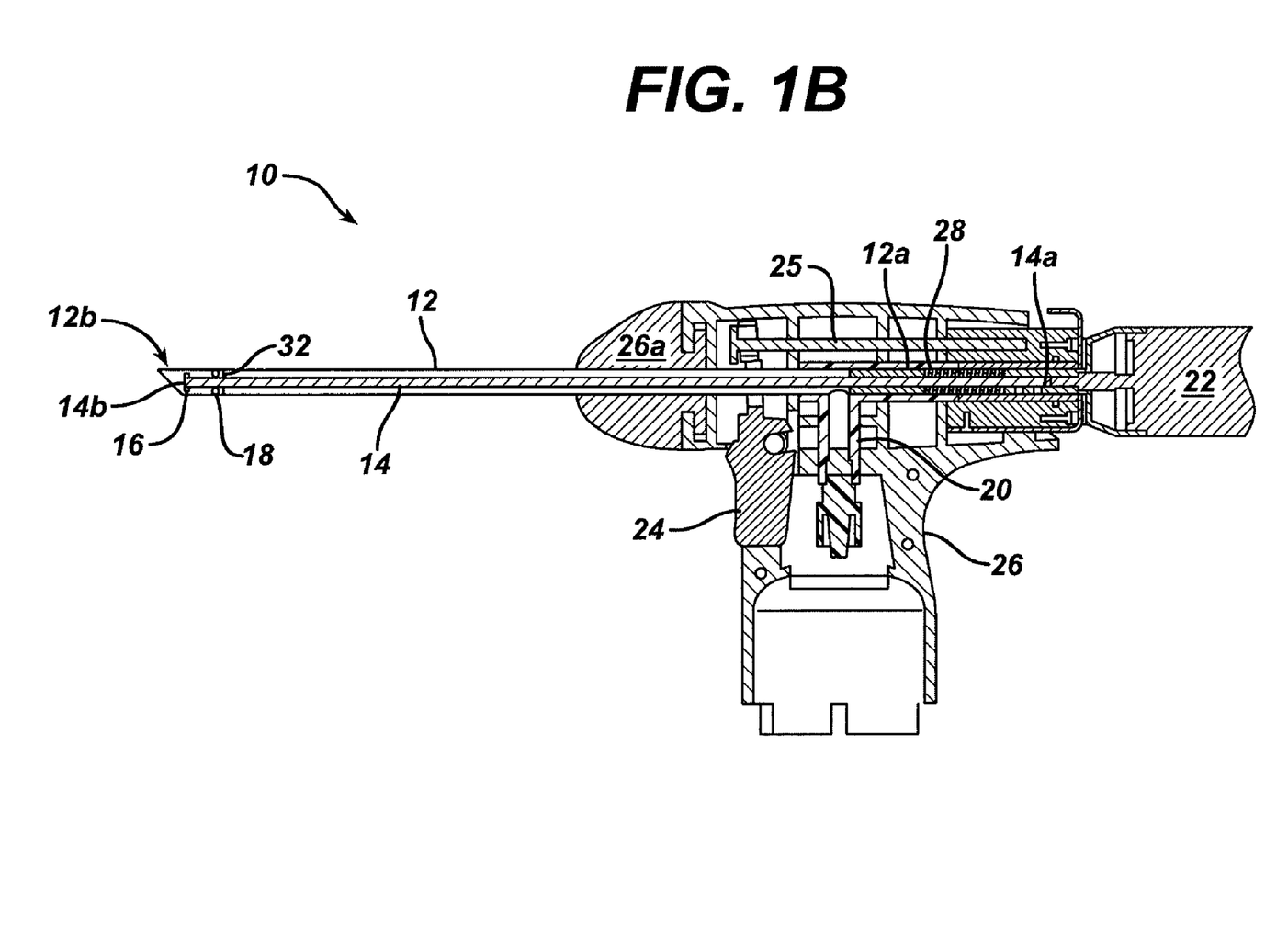
FIG. 1B is a cross-sectional view of the tissue extraction and maceration device shown in FIG. 1A.

The present invention provides devices and methods for extracting and macerating tissue, and optionally for depositing the tissue onto a tissue scaffold. As shown in FIGS. 1A-1B, the device 10 generally includes an outer tube 12 having a substantially open distal end 12b that is adapted to be placed on and preferably to form a seal with a tissue surface, and a shaft 14 (FIG. 1B) rotatably disposed within the outer tube 12. The shaft 14 is movable between a first, proximal position, as shown in FIG. 1B, in which the shaft 14 is fully disposed within the outer tube 12, and a second, distal position (not shown) in which a portion of a distal end 14b of the shaft 14 extends through the opening in the distal end 12b of the outer tube 12. The device 10 also includes a tissue harvesting tip 16 formed on the distal end 14b of the shaft 14 that is effective to excise a tissue sample when the shaft 14 is moved to the distal position, and a cutting member 18 that is coupled to the shaft 14 at a position proximal to the tissue harvesting tip 16. The cutting member 18 is effective to macerate a tissue sample excised by the tissue harvesting tip 16. In an exemplary embodiment, the components of the device 10 are positioned within an outer housing 26 that extends around a portion of the outer tube 12 and that has a shape that facilitates handling of the device 10.

The device is particularly advantageous in that it provides a simple, all-in-one device that can be operated using one hand. The device is designed to effectively remove a viable tissue sample, to control the volume of tissue removed, and to macerate the tissue sample into particles having a predetermined size.

Figure 2A:
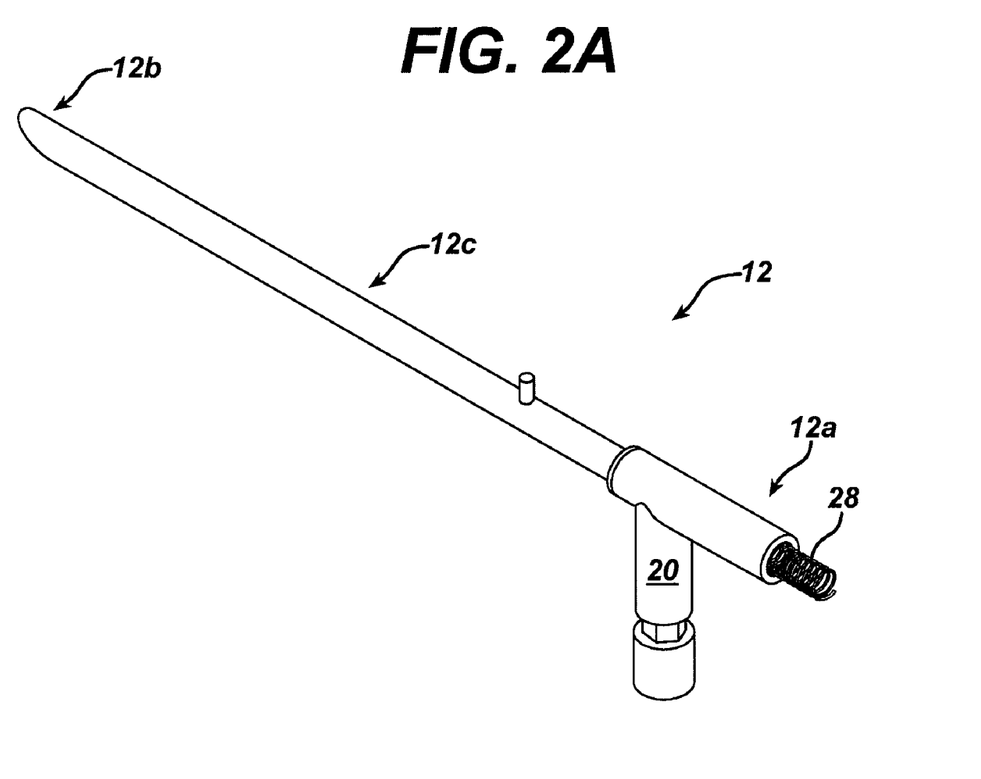
FIG. 2A is a perspective view of the outer tube of the tissue extraction and maceration device shown in FIGS. 1A and 1B.
Figure 2B:
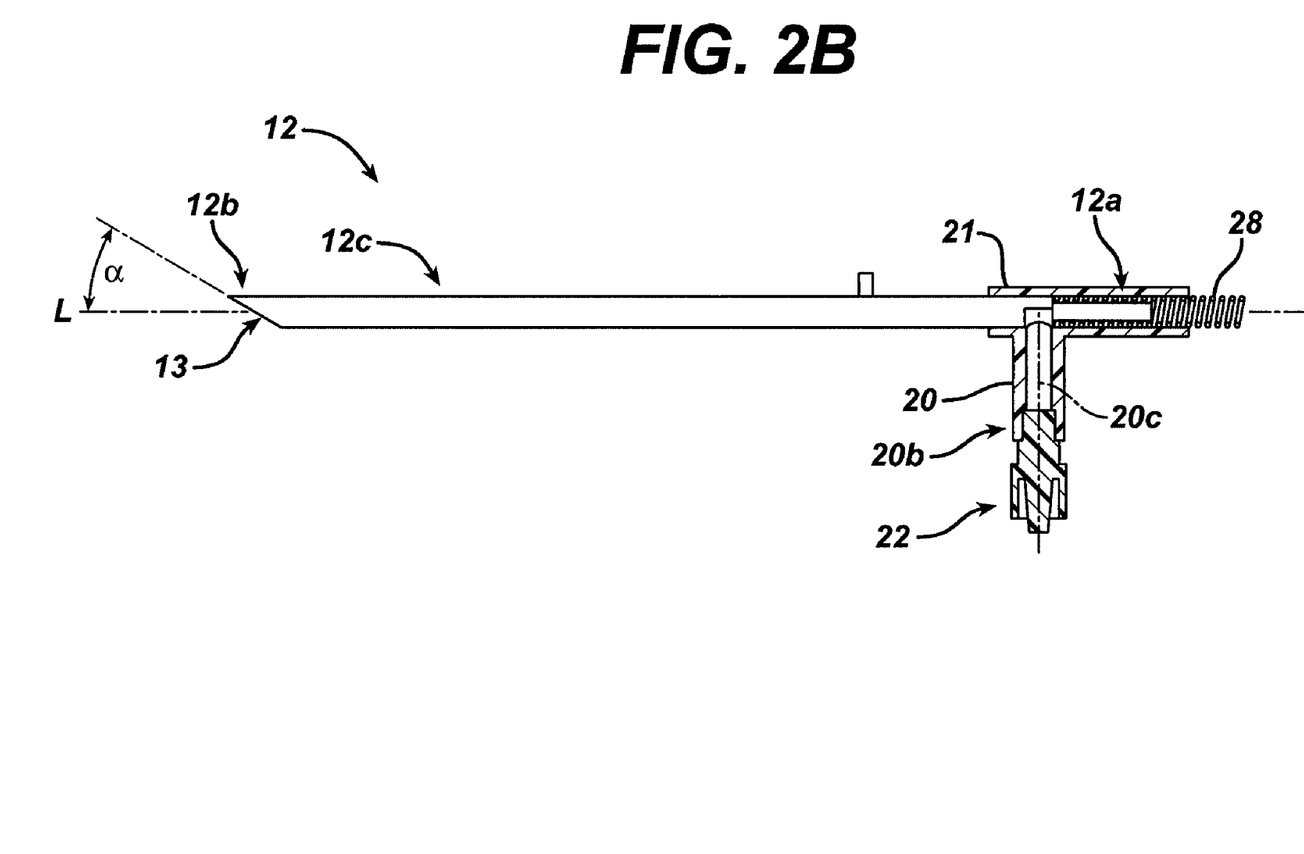
FIG. 2B is a cross-sectional view of the outer tube shown in FIG. 2A.

The outer tube 12 of the device 10, which is shown in more detail in FIGS. 2A and 2B, can have virtually any shape, size, and configuration. In the illustrated embodiment, the outer tube 12 has a generally elongate cylindrical shape and includes proximal and distal ends 12a, 12b with an inner lumen 12c extending therebetween. The proximal end 12a of the outer tube 12 can be open or closed, but it is preferably adapted to connect to a driver mechanism, as will be discussed below. The distal end 12b of the outer tube 12 is at least partially open and it can be adapted to rest against a tissue surface. The distal end 12b can further have a shape that is configured to provide a seal between the inner lumen 12c of the outer tube 12 and a tissue surface. As shown in FIG. 2B, the distal end 12b of the outer tube 12 is disposed at an angle α with respect to a longitudinal axis L of the device 10. While the angle α can vary, in an exemplary embodiment the distal end 12b is angled in the range of about 30° to 70°, and more preferably at about 40° with respect to the axis L. In use, the seal created between the distal end 12b and the tissue surface is particularly advantageous in that it will prevent foreign matter from entering the inner lumen 12c of the outer tube 12. While an angled distal end 12b is preferred, the distal end 12b of the outer tube 12 can have a variety of other configurations, and it can optionally include other features to facilitate placement on and/or a sealed connection with a tissue surface. By way of non-limiting example, the edge wall on the distal end 12b of the outer tube 12 can include surface features, such as ridges 13, formed thereon to facilitate the secure positioning of the outer tube 12 on a tissue surface. A person skilled in the art will appreciate that other techniques can be used to help maintain the position of the outer tube 12 on a tissue surface.

In another embodiment, the outer tube 12 can include a sidearm 20 for mating the device 10 to a tissue collection device, or for otherwise allowing the tissue sample to be collected. The sidearm 20 is preferably disposed adjacent to the proximal end 12a of the device 10, and it preferably extends in a direction substantially transverse to the longitudinal axis L of the tube 12. The sidearm 20 can optionally be coupled to the outer tube 12 by a second tube 21 that extends around a portion of the outer tube 12 and that is attached to the sidearm 20. The sidearm 20 includes an inner lumen 20c that is in communication with the inner lumen 12c of the tube 12, such that all material flowing into the distal end 12b of the tube 12 and through the inner lumen 12c of the tube 12 will enter into the inner lumen 20c in the sidearm 20, rather than exit through the proximal end 12a of the outer tube 12. The distal end 20b of the sidearm 20 can include a connector 22 formed thereon for mating with an entry port formed in a tissue collection device, which will be discussed in more detail with respect to FIG. 6. The connector 22 can have virtually any configuration depending on the type of tissue collection device that the sidearm 20 is adapted to mate to, but the connector 22 should preferably provide a fluid-tight seal between the sidearm 20 and the tissue collection device. The sidearm 20 can also be used to create a vacuum within the device 10 to draw tissue, and any fluid collected with the tissue, through the device 10. The vacuum source can be part of the tissue collection device, or optionally a separate vacuum source can be provided to mate with the sidearm 20. A person skilled in the art will appreciate that the vacuum source can couple to any portion of the outer tube 12, and that the outer tube can have a variety of other shapes, but it should at least be effective to retain a tissue sample therein.

The device 10 can also optionally include an outer housing 26 that extends around a portion of the proximal end 12a of the outer tube 12, and the sidearm 20, to facilitate handling of the device 10. The outer housing 26 can have virtually any shape and size, but it is preferably adapted to fit within a user's hands. In an exemplary embodiment, the outer housing 26 can include a rotating member 26a formed on a distal portion thereof for allowing rotation of the outer tube 12. As shown, the rotating member 26a is rotatably coupled to the housing 26, and it is positioned around and attached to the outer tube 12. As a result, the rotating member 26a can be used to control the position of the distal end 12b of the outer tube 12, thereby facilitating the proper placement of the distal end 12b of the outer tube 12 on a tissue surface. The rotating member 26a is preferably rotatable in a controlled fashion, rather than freely rotatable, such that the position of the outer tube 12 can be maintained during use.

Referring back to FIG. 1B, the device 10 further includes an inner shaft 14 that is disposed within and extends through the outer tube 12. The inner shaft 14 can also have a variety of shapes and sizes, but it is preferably a generally elongate cylindrical member having a proximal end 14a and a distal end 14b. The proximal end 14a of the shaft 14 can extend out of the proximal end 12a of the outer tube to couple to a driver mechanism 22 that is effective to rotate the shaft 14. Virtually any driver mechanism 22 can be used to rotate the shaft 14. As shown in FIG. 1A, and partially shown in FIG. 1B, the driver mechanism 22 is in the form of a motor (not shown) that is disposed within a housing. The motor, e.g., a drill or electric motor system, is effective to rotate the shaft 14. The driver mechanism 22 is preferably only mated to the shaft 14 such that the driver mechanism 22 is movable with the shaft 14 between the proximal and distal positions. In an exemplary embodiment, the motor is preferably operated at a speed that is in the range of about 100 rpm to 5000 rpm. Relatively low operating speeds are preferred to reduce the risk of causing damage to the tissue sample. A person skilled in the art will appreciate that virtually any driver mechanism can be used, and that the speed of the driver mechanism can vary depending on the intended use.

The proximal end 14a of the shaft 14 also includes a trigger mechanism 24 that is effective to move the shaft 14 between the proximal and distal positions. While the trigger mechanism 24 can have a variety of configurations, FIGS. 1A and 1B illustrate a trigger mechanism 24 coupled to the outer housing 26 that is disposed around a portion of the outer tube 12. The trigger mechanism 24 is pivotably disposed within the outer housing 26, and it is coupled to the driver mechanism 22 by a pull rod 25. As a result, when the trigger mechanism 24 is actuated, e.g., using one's finger, the trigger 24 rotates the pull rod 25 to pull the driver mechanism 22 in a distal direction, thereby causing the driver mechanism 22 to move the shaft 14 to the distal position. The shaft 14 preferably moves a distance sufficient to allow only a portion of the distal end 14b of the shaft to extend out of the outer tube 12, as will be discussed in more detail below.

In order to allow the shaft 14 to return to the proximal position after the trigger mechanism 24 is actuated, the device 10 can include a biasing element that is effective to bias the shaft 14 to the proximal position. The biasing element can have a variety of configurations, such as, for example, a spring 28, and it can be coupled to the trigger mechanism 24, the driver mechanism 22, and/or the shaft 14. As shown in FIGS. 1B-2B, the spring 28 is disposed around the proximal end 14a of the shaft 14, and it is positioned just proximal to the proximal end 12a of the outer tube 12. A portion of the spring 28 can optionally be disposed within a second tube 21 which extends around the proximal end 12a of the outer tube 12 to mate the sidearm 20 to the outer tube 12.

In use, the spring 28 is compressed between the driver mechanism 22 and the outer tube 12, thereby creating a biasing force that is effective to push the driver mechanism 22, as well as the inner shaft 14, back into the proximal position. The spring 28 is also effective to create a hard stop between the driver mechanism 22 and the outer tube 12, thereby limiting the distance that the inner shaft 14 can extend from the distal end 12b of the outer tube 12. In an exemplary embodiment, the shaft 14 moves a distance, between the proximal and distal positions, that is in the range of about 1 mm to 5 mm, and more preferably about 3 mm. A person skilled in the art will appreciate that a variety of other techniques can be used to move the shaft 14 between the proximal and distal positions.

Figure 3A:
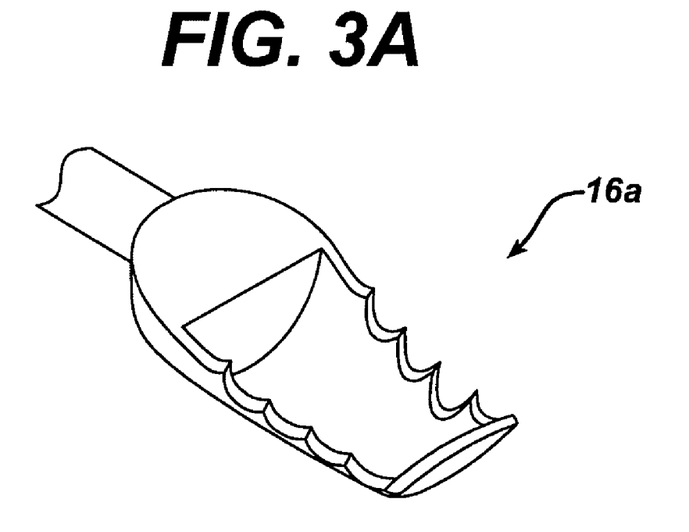
FIG. 3A illustrates one embodiment of a harvesting tip of an inner shaft for use with a tissue extraction and maceration device in accordance with the present invention.
Figure 3B:
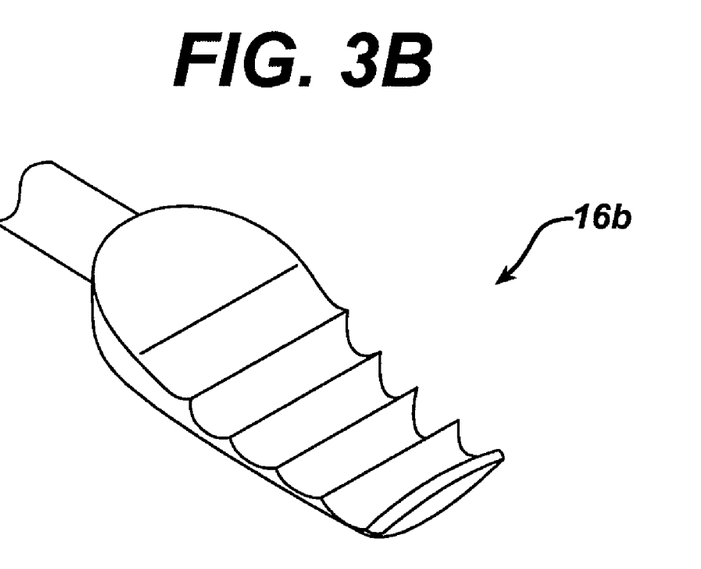
FIG. 3B illustrates another embodiment of a harvesting tip of an inner shaft for use with a tissue extraction and maceration device in accordance with the present invention.
Figure 3C:
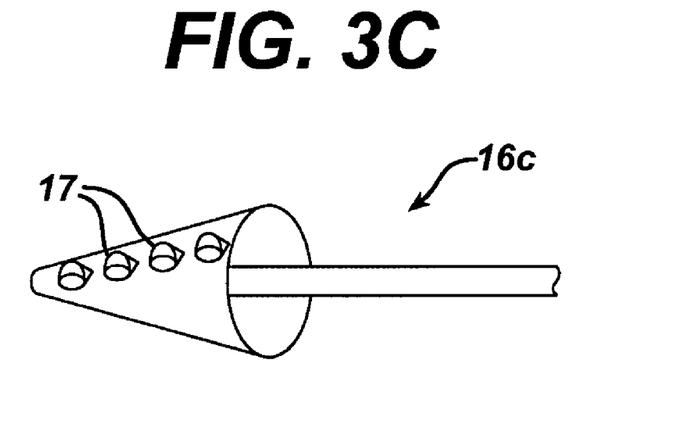
FIG. 3C illustrates yet another embodiment of a harvesting tip of an inner shaft for use with a tissue extraction and maceration device in accordance with the present invention.
Figure 3D:
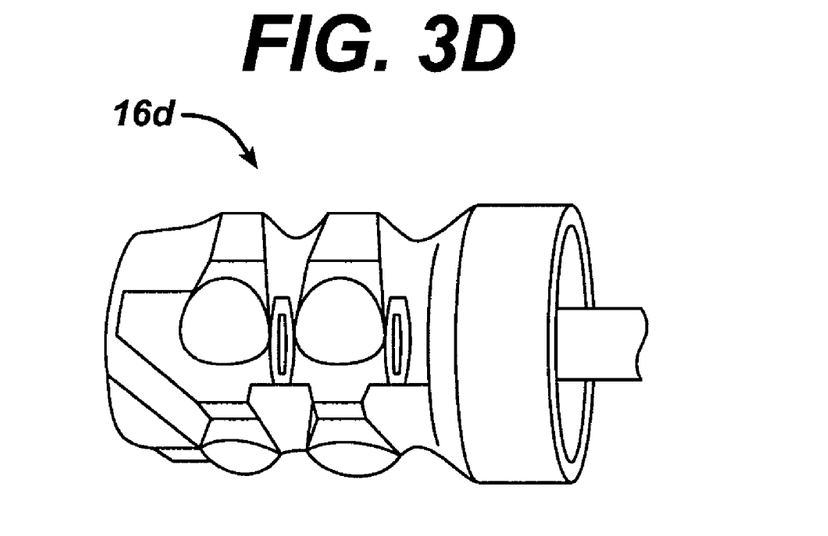
FIG. 3D illustrates yet another embodiment of a harvesting tip of an inner shaft for use with a tissue extraction and maceration device in accordance with the present invention.

The distal end of the inner shaft 14, which is adapted to extend from outer tube 12 when moved into the distal position, preferably includes a tissue harvesting tip 16 that is adapted to retrieve a tissue sample. The tissue harvesting tip 16 can have a variety of configurations, but it is preferably adapted to retrieve a viable tissue sample without tearing or otherwise causing damage to the tissue. More particularly, the tissue harvesting tip 16 should allow for the rapid removal of cleanly cut tissue, rather than crushed or torn tissue. By way of non-limiting example, FIGS. 3A-3D illustrate several embodiments of tissue harvesting tips 16a-d that can be used with the present invention. FIGS. 3A and 3B each illustrate a substantially semi-cylindrical tissue harvesting tip 16a, 16b having a scalloped parameter that is effective to cut into tissue upon rotation of the shaft 14. In FIG. 3A, the tissue harvesting tip 16a is substantially hollow to obtain a larger tissue sample, while in FIG. 3B the tissue harvesting tip 16b is substantially solid and the scallops extend across the surface to form ridges on the harvesting tip 16b. FIGS. 3C and 3D illustrate alternative embodiments of tissue harvesting tips 16c, 16d. In particular, FIG. 3C illustrates a hollow cone-shaped member having several cutting teeth 17 formed around and protruding above an outer surface of the cone-shaped member. The cutting teeth 17 function similar to a cheese grater in that they penetrate the tissue to remove several small tissue samples which are collected inside the hollow cone. FIG. 3D illustrates a tissue harvesting tip 16d that is very similar to the tissue harvesting tip 16c illustrated in FIG. 3C, but that has a substantially cylindrical shape and that includes a substantially flattened distal end.

While the harvesting tip 16 used with the device 10 of the present invention can have a variety of configurations, shapes, and sizes, the harvesting tip 16 is preferably effective to retrieve a predetermined amount of tissue. In an exemplary embodiment, the predetermined volume of tissue, per tissue sample, retrieve by the harvesting tip 16 is in the range of about 0.5 cm$^3$ to 1.5 cm$^3$, and more preferably about 0.9 cm$^3$.

A person skilled in the art will appreciate that a variety of tissue harvesting tips can be used with the present invention, and that FIGS. 3A-3D merely illustrate exemplary embodiments.

Figure 4A:
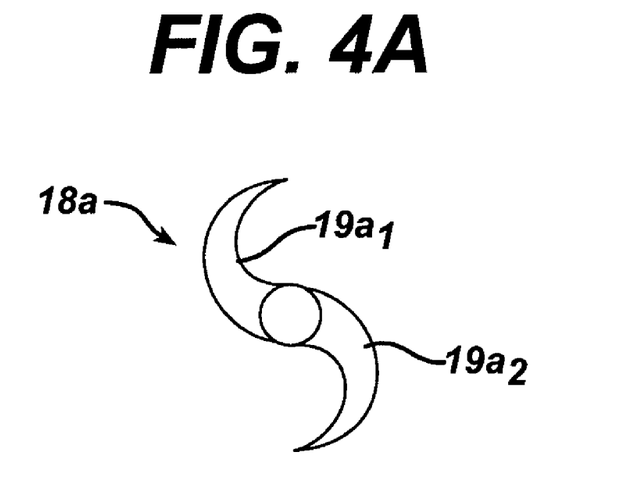
FIG. 4A illustrates one embodiment of a cutting member for use with a tissue extraction and maceration device in accordance with the present invention.
Figure 4B:
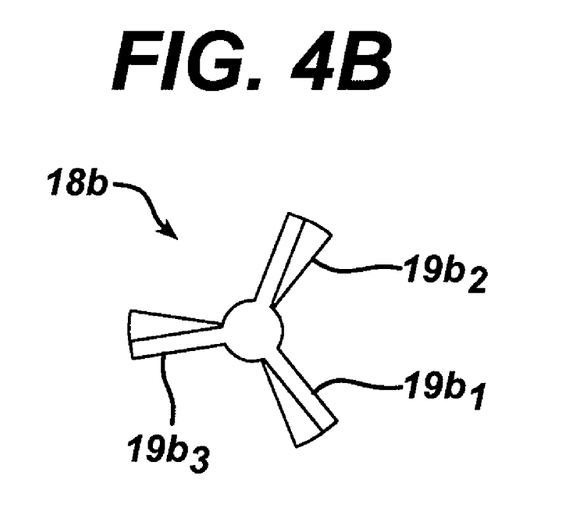
FIG. 4B illustrates another embodiment of a cutting member for use with a tissue extraction and maceration device in accordance with the present invention.
Figure 4C:
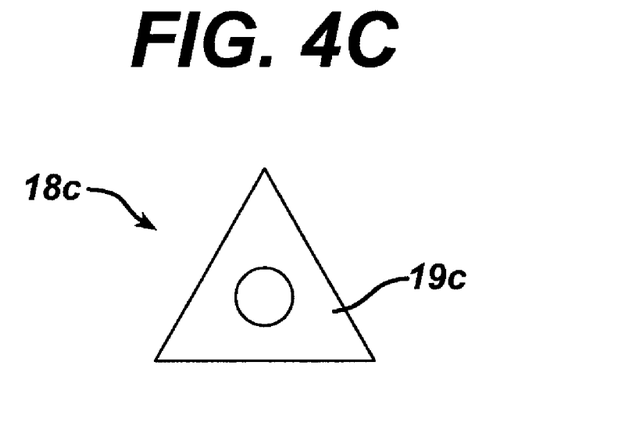
FIG. 4C illustrates yet another embodiment of a cutting member for use with a tissue extraction and maceration device in accordance with the present invention.
Figure 4D:
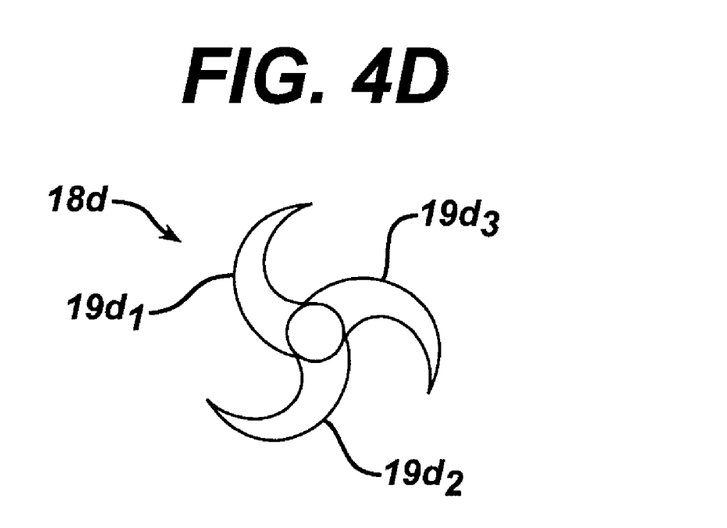
FIG. 4D illustrates yet another embodiment of a cutting member for use with a tissue extraction and maceration device in accordance with the present invention.
Figure 4E:
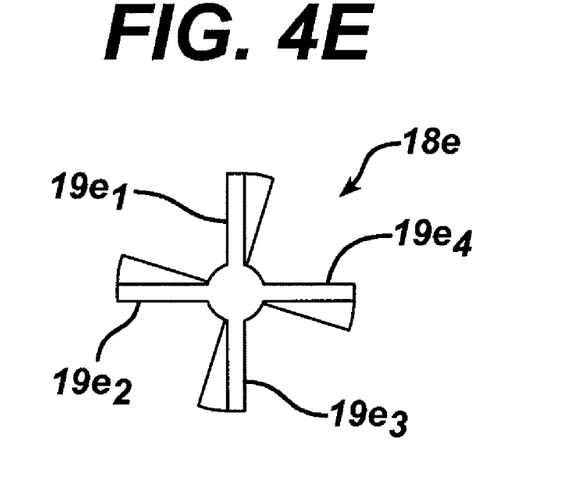
FIG. 4E illustrates yet another embodiment of a cutting member for use with a tissue extraction and maceration device in accordance with the present invention.
Figure 4F:
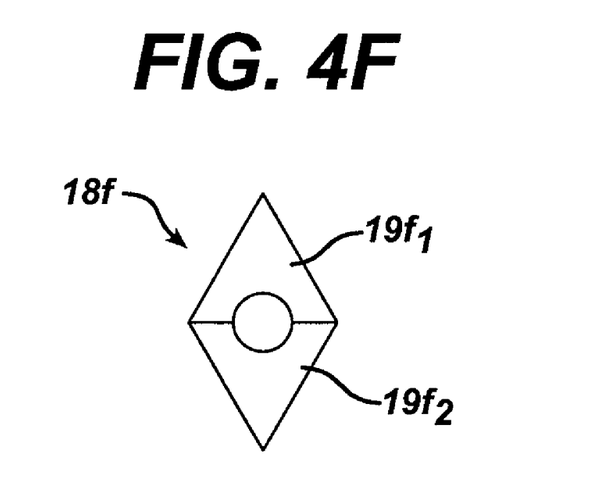
FIG. 4F illustrates yet another embodiment of a cutting member for use with a tissue extraction and maceration device in accordance with the present invention.

The distal end 14b of the shaft 14 can also include a cutting member 18, which is preferably disposed around the shaft 14 at a positioned just proximal to the tissue harvesting tip 16. The cutting member 18 can have a variety of shapes and sizes, but it is preferably effective to macerate the tissue sample excised by the tissue harvesting tip 16. Similar to the tissue harvesting tip 16, the cutting member 18 should be effective to cut, rather than tear, the tissue to allow a viable tissue sample to be obtained. By way of non-limiting example, FIGS. 4A-4F illustrate several embodiments of cutting members 18a-18f that can be used with a device in accordance with the present invention. In general, each cutting member 18a-18f includes one or more blades 19 formed thereon having a particular shape, such as a rectangular shape, a curved shape, a triangular shape, a square shape, or an irregular shape. More particularly, FIG. 4A illustrates a cutting member 18a having two curved or C-shaped blades $19a_1$, $19a_2$ formed thereon; FIG. 4B illustrates a cutting member 18b having three substantially triangular shaped blades $19b_1$, $19b_2$, $19b_3$ extending from the shaft and positioned equidistant from one another; FIG. 4C illustrates a single triangular shaped blade 19c that forms a cutting member 18c; FIG. 4D illustrates a cutting member 18d, similar to cutting member 18a, but having three curved or C-shaped blades $19d_1$, $19d_2$, $19d_3$, formed thereon; FIG. 4E illustrates a cutting member 18e, similar to cutting member 18b, but having four substantially triangular shaped blades $19b_1$, $19b_2$, $19b_3$, $19b_4$ extending from the shaft and positioned equidistant from one another; and FIG. 4F illustrates a cutting member 18f having two triangular blades $19f_1$, $19f_2$ formed thereon. While a variety of cutting elements 18 are illustrated, in an exemplary embodiment, the cutting element is effective to macerate tissue into particles having a diameter in the range of about 0.7 mm to 1.3 mm, and more preferably about 1.0 mm.

Figure 5:
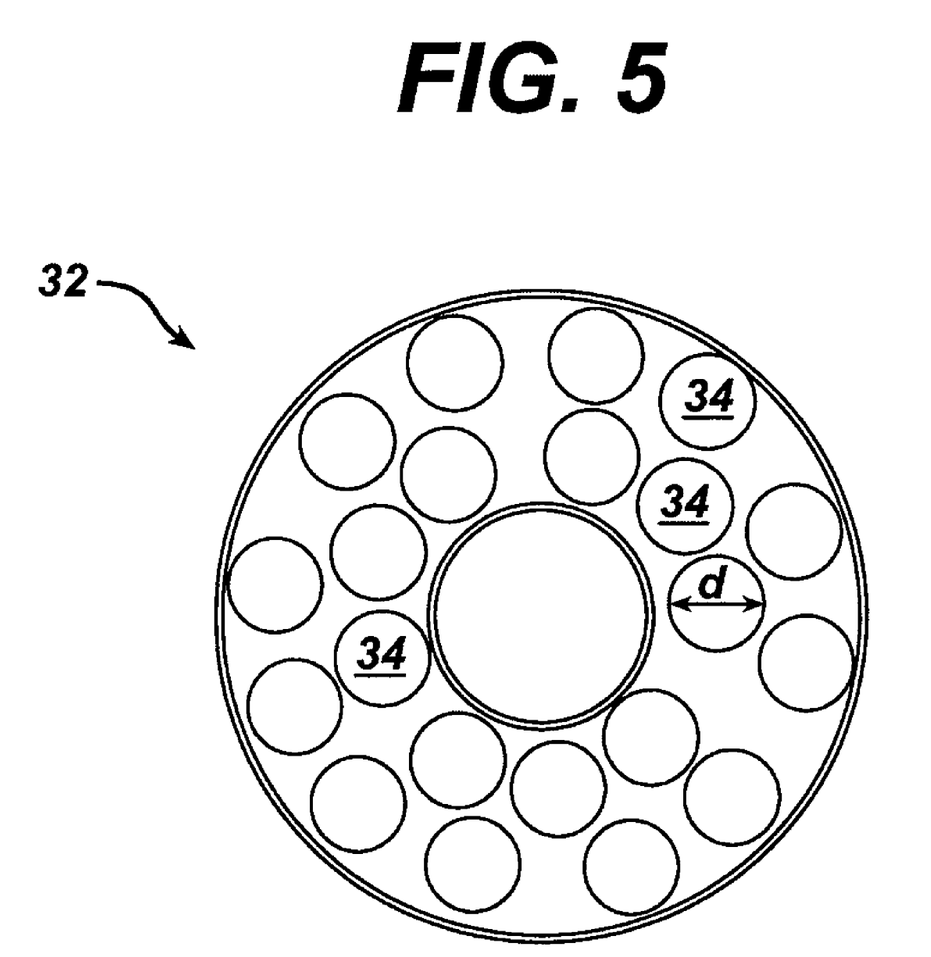
FIG. 5 illustrates one embodiment of a sizing screen for use with a tissue extraction and maceration device in accordance with the present invention.

The device 10 can also optionally include a sizing screen 32, as shown in FIG. 5, that is adapted to control the size of the tissue particles that are allowed to pass through the outer tube 12. The sizing screen 32 is preferably disposed just proximal to the cutting member 18, and it can include several openings 34 formed therein which have a size that permits tissue particles having a size less than the size of the openings 34 to pass therethrough. The openings 34 can vary in shape and size, but in an exemplary embodiment the openings 34 have a diameter d in the range of about 0.7 mm to 1.3 mm, and more preferably about 1.0 mm. As a result, only tissue particles having a size smaller than the size of the openings 34 will be allowed to pass through the sizing screen 32. The remaining tissue particles, which have a size greater than the size of the openings 34, will continue to be excised by the cutting member 18 until they are small enough to pass through the openings 34. To ensure that all of the tissue sample is excised to the appropriate size, the cutting member 18 and the sizing screen 32 are preferably positioned substantially close to one another so that tissue particles being held (preferably by a vacuum force) against the sizing screen 32 will come into contact with the cutting member 18. In another embodiment, the sizing screen 32 can facilitate excising of the tissue sample. In particular, each opening can have an upstream edge that is effective to cut tissue having a size greater than the circumference of the openings.

Figure 7A:
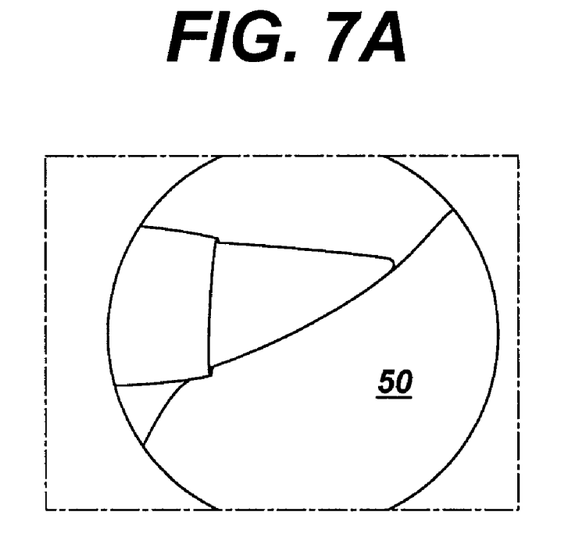
FIG. 7A illustrates a tissue extraction and maceration according to the present invention positioned on a tissue surface.
Figure 7B:
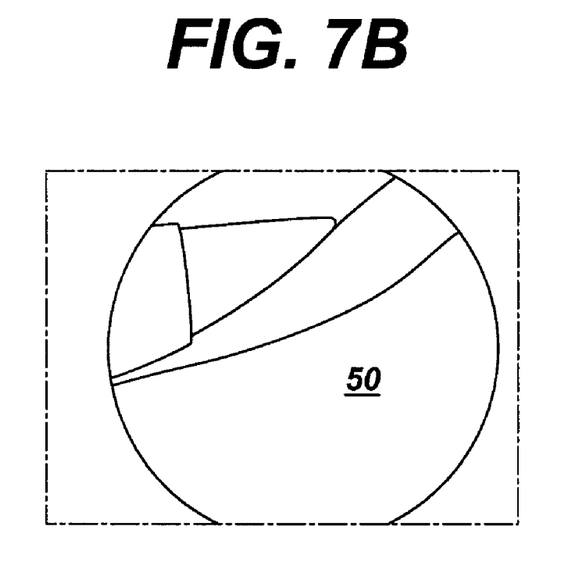
FIG. 7B illustrates the tissue surface having a tissue sample removed therefrom using a tissue extraction and maceration device according to the present invention.

In use, the device 10 is connected to a vacuum source (preferably via the sidearm 20) that is effective to create a vacuum within the inner lumen 12c of the outer tube 12, and the distal end 12b of the outer tube is positioned against tissue surface 50, as shown in FIG. 7A. The motor 22 is activated to rotate the shaft 14, and the trigger 24 is then squeezed to advance the motor 22 and the shaft 14 in a distal direction. As a result, the tissue harvesting tip 16 will extend out of the distal end 12b of the outer tube 12 and into the tissue. Since the shaft 14 is rotating, the tissue harvesting tip 16 will rotate to excise a tissue sample. As the trigger 24 is released, the biasing element 28 causes the shaft 14 to return to the proximal position. The trigger 24 is preferably only actuated once to cause the shaft to rapidly advance into the tissue to obtain a tissue sample. Once the sample is obtained, the vacuum force draws the tissue sample toward the sizing screen 32, where in the rotating cutting member 18 macerates the tissue. Once the macerated particles are small enough to fit through the openings 34 in the sizing screen 32, the particles are drawn through the inner lumen 12b of the outer tube 12, and preferably through the inner lumen 20c in the sidearm 20. Additional samples of tissue can be taken by repositioning the distal end 12b of the outer tube 12 on a tissue surface and actuating the trigger 24 to obtain another sample. FIG. 7B illustrates a tissue surface 50 having a tissue sample removed therefrom, and having the distal end 12b of the outer tube 12 repositioned to obtain a second sample.

Figure 6:
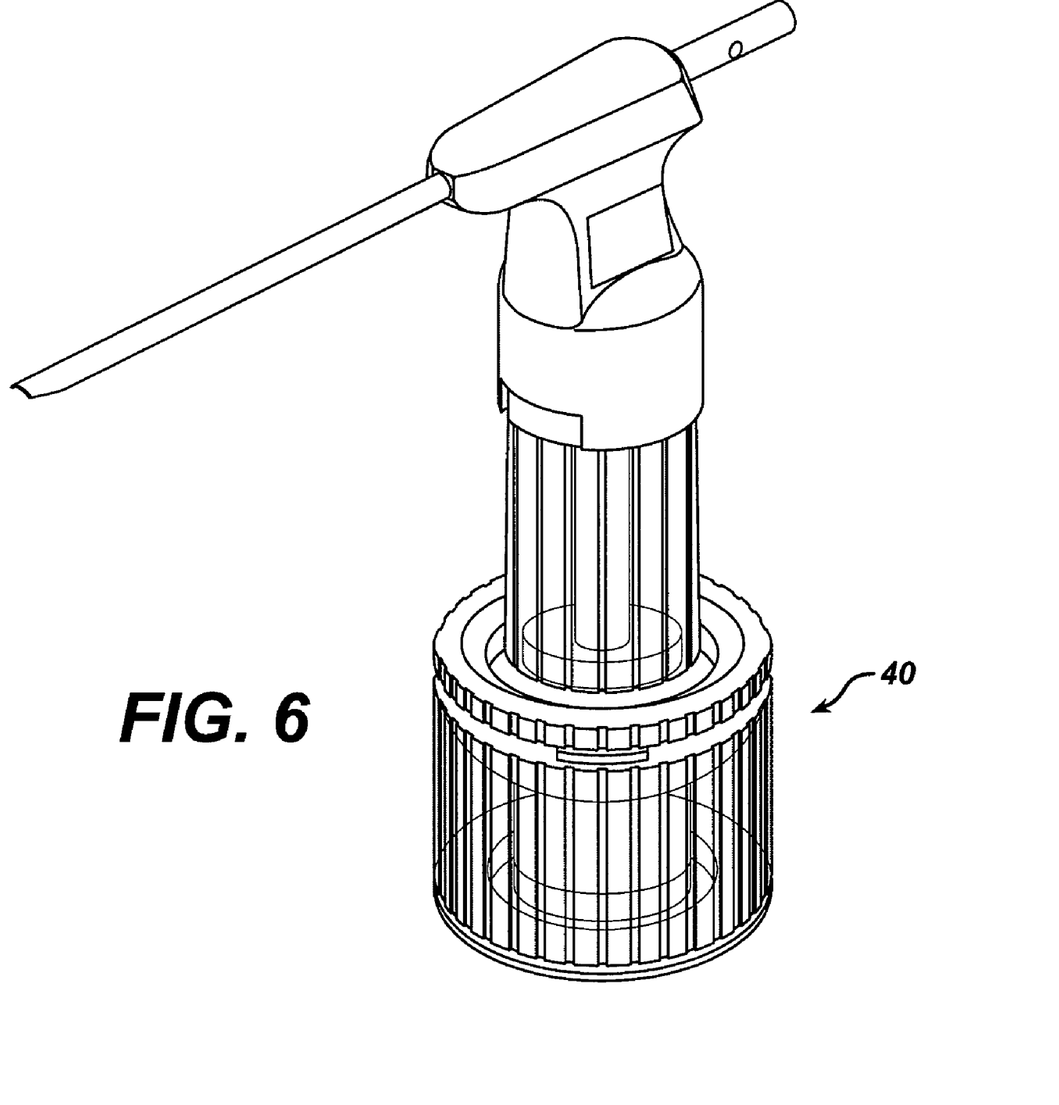
FIG. 6 illustrates the tissue extraction and maceration device shown in FIG. 1A mated to a tissue collection device according to another embodiment of the present invention.

As previously indicated, the tissue sample can be collected into a tissue collection device. While virtually any tissue collection device can be used, FIG. 6 illustrates an exemplary embodiment of a tissue collection device 40. The tissue collection device 40 generally includes a housing having an inner chamber with a tissue scaffold disposed therein. The device 40 is effective to deposit the macerated sample onto the tissue scaffold, and to collect and excess fluid obtained with the tissue sample. The device 40 is described in more detail in U.S. patent application Ser. No. 10/402,266, entitled "Tissue Collection Device and Methods," filed on Mar. 28, 2003, and incorporated herein by reference in its entirety. The combination of the device 10 of the present invention and the tissue collection device 40 is particularly advantageous in that it allows a tissue sample to be excised, macerated, and deposited onto a tissue scaffold in a single step.

The features and other details of the invention will now be more particularly described and pointed out in the claims. It will be understood that the particular embodiments of the invention are shown by way of illustration and not as limitations of the invention. Those skilled in the art will know, or be able to ascertain, using no more than routine experimentation, many equivalents to the specific embodiments of the invention described herein. These and all other equivalents are intended to be encompassed by the following claims.

What is claimed is:
1. A method for harvesting a tissue sample, comprising:
providing a tissue extraction and preparation device having an outer tube with an open distal end, and a shaft rotatably disposed within the outer tube and including a tissue harvesting tip formed on the distal end thereof and a cutting member coupled to the shaft at a position proximal to the tissue harvesting tip;
coupling a proximal end of the shaft to a driver mechanism;
positioning the open distal end of the outer tube against a tissue surface at a desired tissue sample site;
actuating the driver mechanism to effect rotation of the shaft within the outer tube;
moving the shaft from a proximal position, wherein the harvesting tip of the shaft is disposed within the outer tube, to a distal position, wherein the harvesting tip extends distally from the outer tube to penetrate the tissue surface, thereby causing the harvesting tip to obtain a tissue sample;

returning the shaft to the proximal position wherein the tissue sample is macerated by the cutting member; and coupling the outer tube to a tissue dispensing device that is effective to deposit the macerated tissue sample onto a tissue scaffold for subsequent growth.

2. The method of claim 1, further comprising the step of coupling the outer tube to a vacuum pump that is effective to draw the macerated tissue sample through at least a portion of the outer tube.

3. The method of claim 1, wherein the device further includes a biasing element that is effective to bias the shaft to the proximal position.

4. The method of claim 3, wherein the device further includes a trigger mechanism that, upon actuation, is effect to overcome the biasing force to move the shaft from the proximal position to the distal position.

5. The method of claim 1, wherein the macerated tissue passes through a sizing screen before being deposited onto the tissue scaffold.

6. The method of claim 1, wherein the tissue cut by the tissue harvesting tip is larger than the tissue macerated by the cutting member.

7. A method for harvesting a tissue sample, comprising:
positioning an outer tube of a tissue extraction and preparation device against a tissue surface at a desired tissue sample site, the tissue extraction and preparation device having a shaft rotatably disposed within the outer tube;

actuating an actuation mechanism of the device to move the shaft distally relative to the tissue extraction and preparation device such that a distal end of the shaft extends distally past a distal end of the outer tube; and actuating a driver mechanism to excise a tissue sample with a tissue harvesting tip disposed on the shaft, wherein the excised tissue sample is macerated with a cutting member coupled to the shaft proximal to the tissue harvesting tip and is deposited for subsequent growth in a collection device coupled to the tissue extraction and preparation device.

8. The method of claim 7, wherein actuating the actuation mechanism moves the shaft from a position wherein the tissue harvesting tip of the shaft is disposed within the outer tube to a position wherein the tissue harvesting tip extends distally from the outer tube to penetrate the tissue surface.

9. The method of claim 7, further comprising actuating the actuation mechanism to move the shaft proximally relative to the tissue extraction and preparation device such that the distal end of the shaft is disposed within the outer tube.

10. The method of claim 9, wherein the excised tissue sample is macerated with the cutting member while the distal end of the shaft is disposed within the outer tube.

11. The method of claim 7, wherein the driver mechanism coupled to a proximal end of the shaft rotates the shaft during tissue excising and maceration.

12. The method of claim 7, wherein actuating the actuation mechanism of the device to move the shaft distally relative to the tissue extraction and preparation device includes actuating a trigger mechanism that, upon actuation, is effect to overcome a proximal biasing force to move the shaft distally.

13. A method for harvesting a tissue sample, comprising:
actuating a trigger mechanism to move a shaft distally relative to the trigger mechanism and relative to an outer tube disposed around the shaft; and actuating a driver mechanism to rotate the shaft relative to the outer tube such that a tissue harvesting tip contacts tissue to excise a tissue sample, wherein the excised tissue is passed proximally through a cutting element coupled to the shaft proximal to the tissue harvesting tip and macerated by the cutting element for deposition on a tissue scaffold for subsequent growth.

14. The method of claim 13, further comprising actuating the trigger mechanism to move the shaft proximally relative to the trigger mechanism and relative to the outer tube after a tissue sample is excised by the tissue harvesting tip.

15. The method of claim 13, wherein the macerated tissue sample is passed through a sizing screen before deposition onto a tissue scaffold.

16. The method of claim 13, wherein a proximal end of the shaft is coupled to the driver mechanism for rotation thereof.

17. The method of claim 13, wherein actuating the trigger mechanism to move the shaft distally includes moving the shaft from a proximal position, wherein the harvesting tip of the shaft is disposed within the outer tube, to a distal position, wherein the harvesting tip extends distally from the outer tube to penetrate the tissue surface, thereby causing the harvesting tip to obtain a tissue sample.

18. The method of claim 13, further comprising actuating a vacuum pump coupled to the outer tube to draw the excised tissue sample proximally through the cutting element.

19. The method of claim 13, wherein the cutting element remains within the outer tube while the tissue is excised by the tissue harvesting tip.

* * * * *